(12) United States Patent
Gonopolskiy et al.

(10) Patent No.: US 9,002,192 B2
(45) Date of Patent: *Apr. 7, 2015

(54) BREATHABLE PHYSIOLOGICAL SENSOR

(71) Applicant: Covidien LP, Mansfield, MA (US)

(72) Inventors: Oleg Gonopolskiy, West Bloomfield, MI (US); Arik Anderson, Birmingham, MI (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/088,938

(22) Filed: Nov. 25, 2013

(65) Prior Publication Data

US 2014/0081119 A1 Mar. 20, 2014

Related U.S. Application Data

(63) Continuation of application No. 12/779,674, filed on May 13, 2010, now Pat. No. 8,611,976.

(60) Provisional application No. 61/178,277, filed on May 14, 2009.

(51) Int. Cl.
*A61B 5/00* (2006.01)
*A61B 5/1455* (2006.01)

(52) U.S. Cl.
CPC .............. *A61B 5/6832* (2013.01); *A61B 5/0059* (2013.01); *A61B 5/14552* (2013.01); *A61B 5/6833* (2013.01); *A61B 2562/0233* (2013.01); *A61B 2562/043* (2013.01); *A61B 2562/164* (2013.01)

(58) Field of Classification Search
USPC .......................................... 300/310
See application file for complete search history.

(56) References Cited

U.S. PATENT DOCUMENTS

| 5,465,714 | A | 11/1995 | Scheuing |
| 5,584,296 | A | 12/1996 | Cui et al. |
| 5,891,026 | A | 4/1999 | Wang et al. |
| 2006/0276700 | A1 | 12/2006 | O'Neil et al. |
| 2009/0076405 | A1 | 3/2009 | Amurthur et al. |
| 2011/0275972 | A1 | 11/2011 | Rosenberg |

FOREIGN PATENT DOCUMENTS

| EP | 0756847 | 2/1997 | |
| EP | 756847 A1 * | 2/1997 | ............... A61B 5/00 |
| WO | WO-9412096 | 6/1994 | |
| WO | WO-9427494 | 12/1994 | |
| WO | WO-2009036327 | 3/2009 | |

* cited by examiner

*Primary Examiner* — Clayton E Laballe
*Assistant Examiner* — Noam Reisner
(74) *Attorney, Agent, or Firm* — Harness, Dickey & Pierce, PLC

(57) ABSTRACT

A sensor includes a sensor pad that allows air and moisture to diffuse from a patient's skin. A light source is disposed on the sensor pad is configured to generate near-infrared light. A light detector disposed on the sensor pad is configured to detect near-infrared light generated by the light source.

14 Claims, 2 Drawing Sheets

BREATHABLE PHYSIOLOGICAL SENSOR

CROSS-REFERENCE TO RELATED APPLICATIONS

This application is a continuation application of U.S. Ser. No. 12/779,674 filed on May 13, 2010, which claims priority to U.S. Ser. No. 61/178,277 filed on May 14, 2009, the contents of which are incorporated herein in their entirety.

BACKGROUND

Physiological sensors are often used in medical applications to help doctors diagnose, monitor, and treat patients. A physiological sensor employing near-infrared spectroscopy may be used to detect characteristics of various body tissues by transmitting and receiving near-infrared light through the body tissue and outputting a signal to a controller that provides valuable information about the body tissue. These physiological sensors include electronic components that are sensitive to moisture and can be damaged by body fluids. To prevent damage caused by body fluids, the electronic components are surrounded by layers of an elastic material.

This elastic material and the adhesives used to adhere the sensor to the patient's skin restrict airflow and moisture transfer from the patient's skin, which can cause skin damage and provide ideal conditions for bacterial growth. Patients with fragile skin are especially susceptible to the skin damage caused by these types of sensors. For instance, a neonate's skin needs air for development and sensors that restrict airflow and moisture transfer impede skin development. Accordingly, a sensor is needed that allows air and moisture to diffuse from the patient's skin.

DETAILED DESCRIPTION

An exemplary sensor includes a light source that generates near-infrared light and a light detector that detects the light as it passes through body tissue. The light source and the light detector are disposed on a sensor pad that allows air and moisture to diffuse from a patient's skin. This diffusion of air and moisture helps improve skin development and reduces the opportunity for bacterial growth, especially if the sensor is adhered to the patient for a long time. Thus, the sensor described herein may be beneficial to all patients to which a physiological sensor is applied, and especially beneficial to neonates and other patients with sensitive skin.

Figure 1:
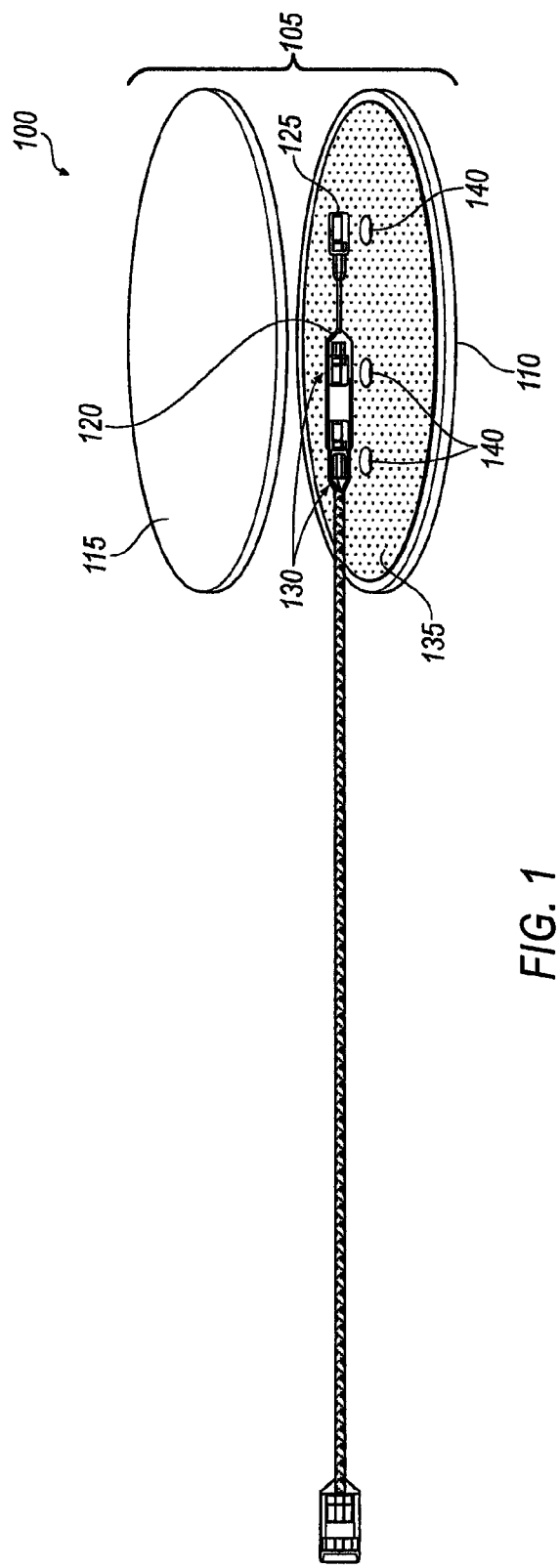
FIG. 1 is an assembly view of an exemplary physiological sensor.

FIG. 1 illustrates an assembly view of an exemplary sensor 100 that allows air and moisture to diffuse from a patient's skin. The sensor 100 may take different forms and include multiple or alternative components. While an exemplary sensor 100 is illustrated in FIG. 1, the components illustrated are merely exemplary and not intended to be limiting. Indeed, additional or alternative components and/or implementations may be used.

Referring to FIG. 1, an exemplary sensor 100 includes a sensor pad 105 having a bottom layer 110 and a top layer 115. The sensor pad 105 partially houses a circuit board 120 having at least one light source 125 and at least one light detector 130. The exemplary sensor 100 may be placed on a patient's skin to, for example, determine the level of oxygen saturation in the patient's blood or a specific body tissue.

The sensor pad 105 allows air and moisture to diffuse from a patient's skin. The bottom layer 110 and top layer 115 may be formed from a breathable material such as an open cell foam. The open cell foam may include any polyurethane foam that is breathable and opaque to near-infrared light. For instance, the open cell foam may be black Poron® foam.

The bottom layer 110 of the sensor pad 105 is the part of the sensor 100 that may be placed on the patient's skin. In one exemplary approach, only the bottom layer 110 is formed from the breathable material. For instance, the bottom layer 110 may have a thickness that is sufficient to allow lateral diffusion of airflow and moisture from the patient's skin. In this instance, it is not necessary that the top layer 115 allow air to diffuse. Therefore, the top layer 115 does not need to be formed from the breathable material so long as the lateral diffusion through the bottom layer 110 is sufficient. Whether the thickness of the bottom layer 110 is sufficient for lateral diffusion may depend upon the type of material that forms the bottom layer 11. In one exemplary approach, the bottom layer 110 with a thickness of 1-2 mm may be sufficient for lateral diffusion if the bottom layer 110 is a polyurethane open cell foam with a cell size of 0.2-0.5 mm. Of course, these cell sizes and thicknesses are merely exemplary and the bottom layer 110 may have a different thickness for lateral diffusion. For example, the thickness of the bottom layer 110 that is sufficient for lateral diffusion may change depending on the type and cell size of material forming the bottom layer 110.

The bottom layer 110 and top layer 115 may be adhered to one another with a breathable adhesive 135. The breathable adhesive 135 may include a porous material that allows a minimum amount of air to flow between the bottom layer 110 and the top layer 115. This way, the breathable adhesive 135 will not significantly inhibit the diffusion of air and moisture from the patient's skin. Instead, the breathable adhesive 135 allows air and moisture to travel between the bottom layer 110 and the top layer 115. Examples of the breathable adhesive 135 include adhesives MH-92295-990 or MH-92174-990 from Adhesives Research Inc. Another breathable adhesive 135 may include a silicon adhesive.

The sensor pad 105 may be attached to the patient's skin by applying a pressure sensitive adhesive to the portion of the bottom layer 110 that touches the patient's skin. If the pressure sensitive adhesive is breathable (e.g., does not significantly inhibit the flow of air and moisture from the patient's skin), then the pressure sensitive adhesive may cover the entire portion of the bottom layer 110 that touches the patient's skin. However, if the pressure sensitive adhesive is not breathable, the pressure sensitive adhesive may be applied to only part of the portion of the bottom layer 110 to reduce the area of the patient's skin that is covered by the pressure sensitive adhesive.

One alternative to using a pressure sensitive adhesive may be to use a breathable harness. The breathable harness may include, for instance, a breathable cotton strap that does not significantly prevent the diffusion of air and moisture across the patient's skin. Another alternative may be to attach the sensor pad 105 to the patient's skin with a porous skin barrier, such as a silicone adhesive with holes that allow gas permeation from the patient's skin to the bottom layer 110. An example of this includes a Mepitel® wound dressing, which has holes that allow breathability.

Figure 2:
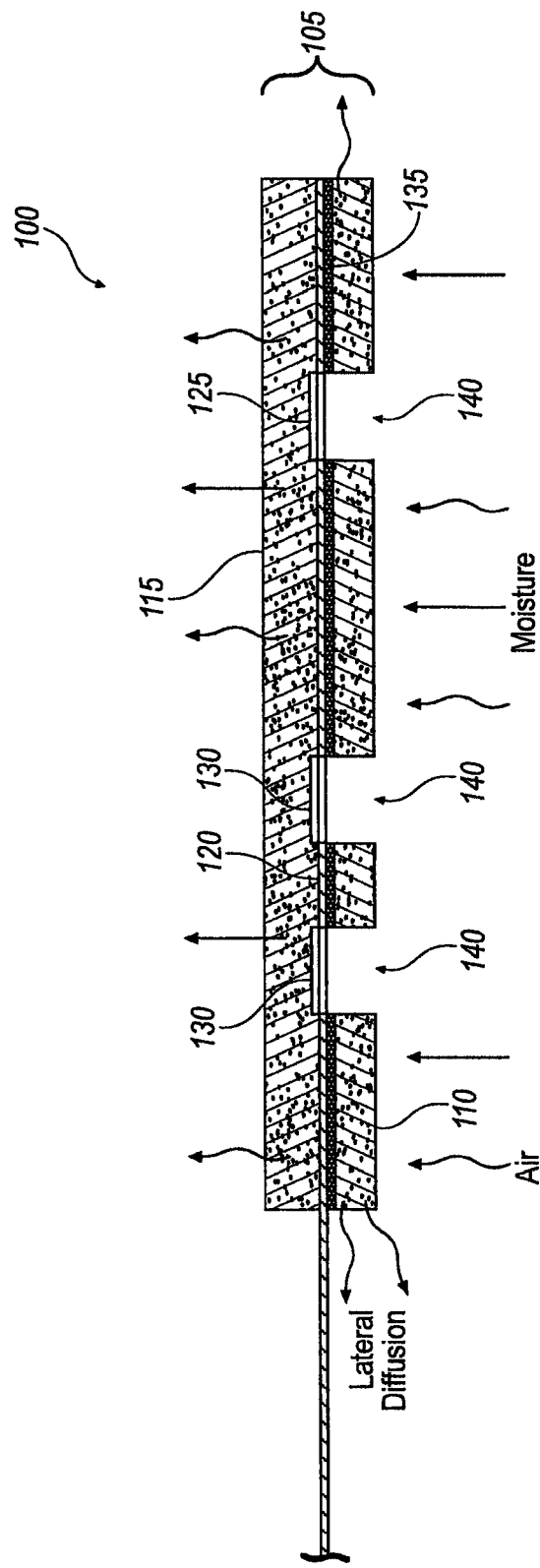
FIG. 2 is an exemplary side cross-sectional view of the exemplary physiological sensor of FIG. 1.

The circuit board 120 is at least partially disposed on the sensor pad 105. As illustrated, the circuit board 120 is sandwiched between the top layer 115 and the bottom layer 110. In one exemplary approach, the circuit board 120 may be a flexible printed circuit board so that the circuit board 120 may conform to the shape of the part of the patient's body to which the sensor 100 is applied. In FIGS. 1 and 2, the light source 125 and light detectors 130 are disposed on the same circuit board 120 and sensor pad 105. However, in one exemplary implementation, the light source 125 and light detector 130 may be disposed on different circuit boards 120 on the same sensor pad 105 or different sensor pads 105. Moreover, the circuit board 120 may include any number of light sources 125 and/or light detectors 130 as well as other components such as resistors, capacitors, transistors, amplifiers, etc.

The light source 125 may include any device configured to generate light in the near-infrared region of the electromagnetic spectrum and propagate the light through, for example, part of a patient's body such as blood or organic tissue. The light source 125 may include a light emitting diode, a laser or laser diode, an optical fiber, etc. Any number of light sources 125 may be used with each light source 125 outputting light at the same or different wavelengths or ranges of wavelengths.

The light detector 130 may include any device configured to receive light generated by the light source 125 in the near-infrared region of the electromagnetic spectrum after the light has propagated through part of a patient's body such as blood or organic tissue. The light detector 130 may include a photodiode. The sensor 100 may include any number of light sources 125. In one exemplary implementation, the sensor 100 may include one light detector 130 for each light source 125. In another exemplary implementation, the sensor 100 may include one light detector 130 that receives light from multiple light sources 125. Alternatively, the sensor 100 may include multiple light detectors 130 that receive light from a single light source 125.

The light source 125 and light detector 130 may be disposed on the circuit board 120 between the top layer 115 and the bottom layer 110 of the sensor pad 105. For light to reach the patient, travel through blood or tissue, and be received by the light detector 130, the light source 125 and the light detector 130 may be disposed over one or more openings 140 defined by the bottom layer 110 of the sensor pad 105. As previously mentioned, the bottom layer 110 may be opaque to near-infrared light. Therefore, the openings 140 provide a way for the light to travel from the light source 125 through the patient's tissue and to the light detector 130. In addition, the breathable adhesive 135 may further define holes aligned with the openings 140 in the bottom layer 110 to allow light to travel from the light source 125 to the light detector 130. For instance, if the breathable adhesive 135 includes the silicon adhesive, the silicon adhesive may define the holes.

The circuit board 120 may be coated with, for instance, a water protective coating to prevent moisture from the patient from damaging the light source 125, light detector 130, or other components disposed on the circuit board 120. The water protective coating may include, for instance, a parylene film. Further, the circuit board 120, the components disposed on the circuit board 120, and the water protective coating may be the only portions of the sensor 100 that inhibit airflow. For this reason, in one exemplary approach, the circuit board 120 is as small as possible.

FIG. 2 is an exemplary cross-sectional view of the exemplary sensor 100 depicted in FIG. 1 placed on a patient's skin. If the adhesive between the top layer 115 and the bottom layer 110 is not porous (e.g., not the breathable adhesive 135), such as an acrylic tape adhesive, then the bottom layer 110 may be sufficiently thick to allow air and moisture to diffuse from the patient's skin through the sides of the bottom layer 110. However, as illustrated in FIG. 2, if the adhesive between the bottom layer 110 and the bottom layer 110 is the breathable adhesive 135, then air will also diffuse from the skin through the top layer 115.

The above description is intended to be illustrative and not restrictive. Many alternative approaches or applications other than the examples provided would be apparent to those of skill in the art upon reading the above description. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. In sum, it should be understood that the invention is capable of modification and variation and is limited only by the following claims.

The present embodiments have been particularly shown and described, which are merely illustrative of the best modes. It should be understood by those skilled in the art that various alternatives to the embodiments described herein may be employed in practicing the claims without departing from the spirit and scope as defined in the following claims. It is intended that the following claims define the scope of the invention and that the method and apparatus within the scope of these claims and their equivalents be covered thereby. This description should be understood to include all novel and non-obvious combinations of elements described herein, and claims may be presented in this or a later application to any novel and non-obvious combination of these elements. Moreover, the foregoing embodiments are illustrative, and no single feature or element is essential to all possible combinations that may be claimed in this or a later application.

All terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary.

The invention claimed is:

1. A sensor comprising:
   a sensor pad having a bottom surface configured to be applied to a patient and a top surface opposite said bottom surface, wherein at least a portion of said sensor pad is formed from a breathable material in a configuration such that air and moisture diffuse laterally from said sensor pad at a rate greater than any diffusion of air and moisture through said top surface;
   a light source disposed on the sensor pad and configured to generate near-infrared light; and
   a light detector disposed on the sensor pad and configured to detect near-infrared light generated by the light source.

2. The sensor of claim 1, wherein said sensor pad comprises a top layer and a bottom layer.

3. The sensor of claim 2, wherein said top layer is coupled to said bottom layer by an adhesive.

4. The sensor of claim 3, wherein said adhesive is breathable.

5. The sensor of claim 2, wherein at least a portion of said bottom layer is formed from said breathable material.

6. The sensor of claim 5, wherein said top layer is not breathable.

7. The sensor of claim 1, wherein said breathable material is a foam material.

8. The sensor of claim 1, wherein said breathable material is an open cell material.

9. The sensor of claim 1, further comprising a breathable adhesive applied to said bottom surface and configured to adhere said sensor pad to the patient.

10. The sensor of claim 1, wherein a thickness of the open cell breathable material is approximately 1.0 mm-2.0 mm.

11. The sensor of claim 1, wherein said breathable material is an open cell material having a thickness and a cell size configured relative to each other to laterally diffuse air and moisture from the patient's skin at a rate that is equivalent to at least a lateral diffusion rate achieved by a polyurethane open cell foam with a cell size of 0.2-0.5 mm and a thickness of 1-2 mm.

12. A sensor comprising:
   a sensor pad at least partially formed from an open cell breathable material having a thickness and a cell size configured relative to each other to laterally diffuse air and moisture from a patient's skin at a rate that is equivalent to at least a lateral diffusion rate achieved by a polyurethane open cell foam with a cell size of 0.2-0.5 mm and a thickness of 1-2 mm;
   a light source disposed on the sensor pad and configured to generate near-infrared light; and
   a light detector disposed on the sensor pad and configured to detect near-infrared light generated by the light source.

13. The sensor of claim 12, wherein said sensor pad comprises a top layer and a bottom layer, said bottom layer being configured to be coupled to a patient.

14. The sensor of claim 13, wherein at least said bottom layer comprises said open cell breathable material.

* * * * *